United States Patent
Huang et al.

(10) Patent No.: US 8,757,005 B2
(45) Date of Patent: Jun. 24, 2014

(54) TESTING MODULE

(75) Inventors: Teng-Tsung Huang, New Taipei (TW);
Yong-Bing Hu, Shenzhen (CN);
Zhang-Sheng Yan, Shenzhen (CN);
Zhan Shang, Shenzhen (CN);
Gong-Shui Cheng, Shenzhen (CN)

(73) Assignees: Hong Fu Precision Industry (ShenZhen) Co., Ltd., Shenzhen (CN);
Hon Hai Precision Industry Co., Ltd., New Taipei (TW)

( * ) Notice: Subject to any disclaimer, the term of this patent is extended or adjusted under 35 U.S.C. 154(b) by 264 days.

(21) Appl. No.: 13/275,449

(22) Filed: Oct. 18, 2011

(65) Prior Publication Data
US 2012/0227506 A1  Sep. 13, 2012

(30) Foreign Application Priority Data
Mar. 10, 2011 (CN) .......................... 2011 1 0057668

(51) Int. Cl.
*G01N 3/02* (2006.01)
(52) U.S. Cl.
USPC ........................................... 73/856

(58) Field of Classification Search
USPC .................................. 73/760, 855, 865, 856
See application file for complete search history.

(56) References Cited

U.S. PATENT DOCUMENTS

| | | | | |
|---|---|---|---|---|
| 4,586,379 A | * | 5/1986 | Burkhardt, Jr. | 73/622 |
| 6,994,436 B2 | * | 2/2006 | Harris | 352/243 |
| 8,200,299 B2 | * | 6/2012 | Lim | 455/575.4 |
| 8,369,076 B2 | * | 2/2013 | Chuang et al. | 361/679.27 |
| 8,521,241 B2 | * | 8/2013 | Zhou et al. | 455/575.4 |

* cited by examiner

*Primary Examiner* — Max Noori
(74) *Attorney, Agent, or Firm* — Novak Druce Connolly Bove + Quigg LLP

(57) ABSTRACT

A very versatile testing module includes a main body, a drive module, a sliding module, a transmission module, and a frictional member. The drive module is positioned in the main body. The transmission module includes a rotational plate and a connecting plate. The drive module drives the rotational plate to rotate. One end of the connecting plate attached to the sliding module, and the other end thereof adjustably attached to the rotational plate. The frictional member is mounted to the sliding module.

10 Claims, 6 Drawing Sheets

TESTING MODULE

BACKGROUND

1. Technical Field

The present disclosure relates to testing modules, and particularly to a testing module for testing the wear-resisting property of portable electronic device.

2. Description of Related Art

The outer surfaces of portable electronic devices (e.g., mobile phones) need to be able to withstand wear and tear. Thus, the wear-resisting property should be tested e.g., to ensure the portable electronic devices keeps a good appearance for some time.

A known testing apparatus includes a frictional member. The frictional member is driven to move repeatedly on the outer surfaces of the tested product in a predetermined time to judge the wear-resisting property of the product surface. However, this known testing module cannot change the movement stroke, and only can test a particular portable electronic device with a fixed size or shape. Each particular testing apparatus corresponds to one kind of portable electronic device which has a particular size or shape. Thus, during the process of testing, a plurality of testing apparatuses is inevitably implemented to test various kinds of portable electronic devices. It results in high costs and decreases the efficiency of the whole test.

Therefore, there is room for improvement within the art.

BRIEF DESCRIPTION OF THE DRAWINGS

Many aspects of the testing module can be better understood with reference to the following drawings. The components in the drawings are not necessarily drawn to scale, the emphasis instead being placed upon clearly illustrating the principles of the testing module. Moreover, in the drawings, like reference numerals designate corresponding parts throughout the several views.

DETAILED DESCRIPTION

Figure 1:
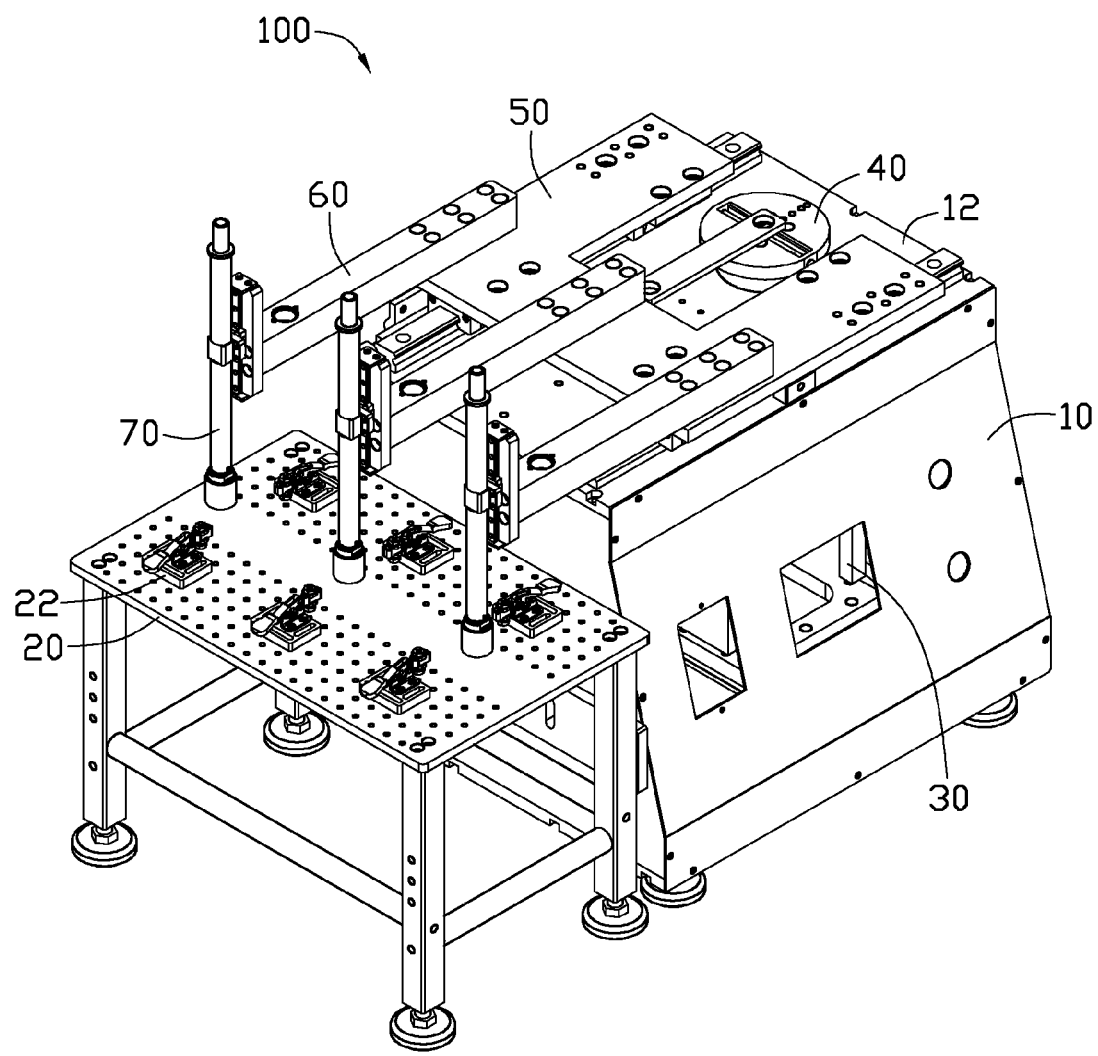
FIG. 1 is a view of one embodiment of an assembled testing module.
Figure 2:
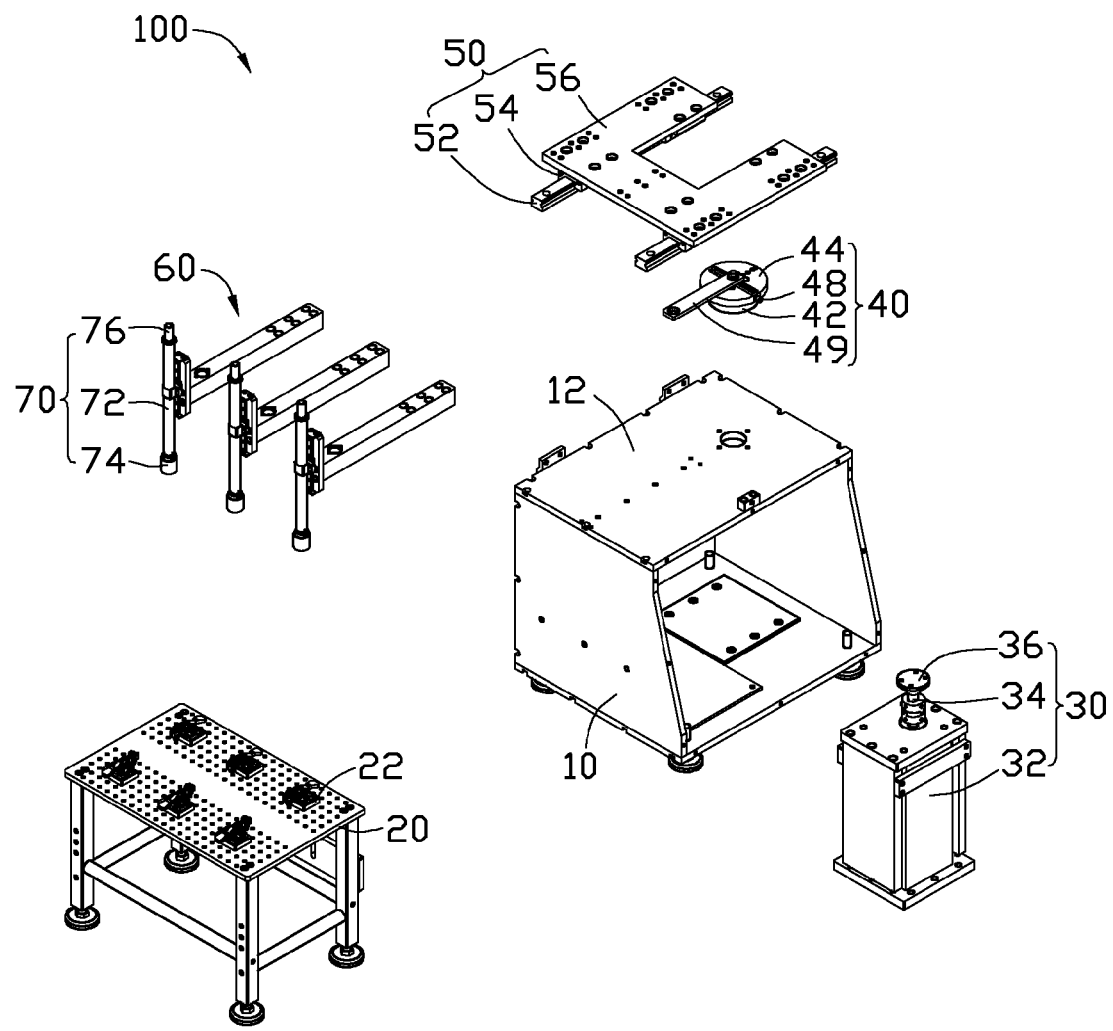
FIG. 2 is an exploded, isometric view of the testing module shown in FIG. 2.

The testing module 100 shown in FIGS. 1 and 2 can be suitably used for testing, amongst other things, the outer surfaces of the housings of mobile phones. The testing module 100 embodied in FIG. 1 includes a main body 10, a worktable 20, a drive module 30, a transmission module 40, a sliding module 50, a number of connecting modules 60, and a number of frictional members 70. The worktable 20 is positioned at one side of the main body 10. The drive module 30 is mounted in the main body 10. The main body 10 includes a top plate 12, and the transmission module 40, the sliding module 50 is positioned on the top plate 12.

A number of clamping members 22 are positioned on the worktable 20. Each clamping member 22 is in two parts, opposite to each other, for clamping the tested product.

The drive module 30 includes a motor 32, a rotor 34, and a latching member 36. The latching member 36 is formed on one end of the rotor 34. When the motor 32 runs, the rotor 34 rotates, which rotates the latching member 36. The latching member 36 extends through the top plate 12, and is connected to the transmission module 40 for driving the transmission module 40 to rotate, and the transmission module 40 transforms rotary motion into linear reciprocating motion.

Figure 3:
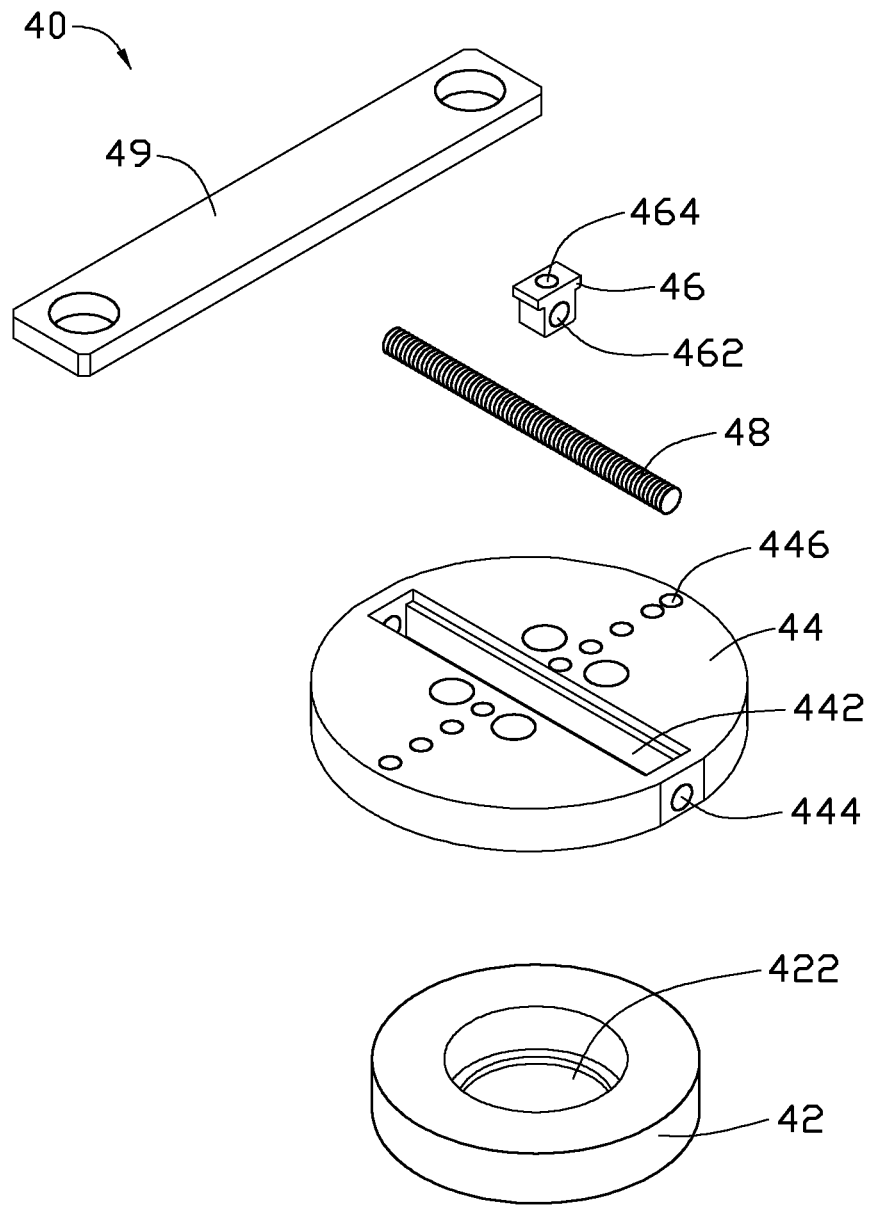
FIG. 3 is an exploded, isometric view of the transmission module contained in FIG. 2.

Referring to FIG. 3, the transmission module 40 includes a support ring 42, a rotational plate 44, a nut 46, a bolt 48 and a connecting plate 49. The support ring 42 is mounted on the top plate 12. The rotational plate 44 is disposed on the support ring 42. The latching member 36 extends through a central hole 422 of the support ring 42, and is mounted to the rotational plate 44 by fasteners. A groove 442 is diametrically defined along the rotational plate 44, but is shorter than the overall diameter of the rotational plate 44. A through hole 444 is defined at each side of the rotational plate 44, and communicates with opposite ends of the groove 442. A number of adjusting holes 446 are defined in the rotational plate 44. The adjusting holes 446 are arranged at different distances, in a line perpendicular to the groove 442.

The nut 46 is substantially T-shaped, and is slidably received in the groove 442. The nut 46 defines a threaded hole 462 and a latching hole 464. The axis of the threaded hole 462 is parallel with the groove 442 and perpendicular to that of the latching hole 464. The bolt 48 is inserted into the through hole 444 and the groove 442, and is screwed into the threaded hole 462. The bolt 48 can be rotated to adjust the location of the nut 46 relative to the rotational plate 44.

Figure 4:
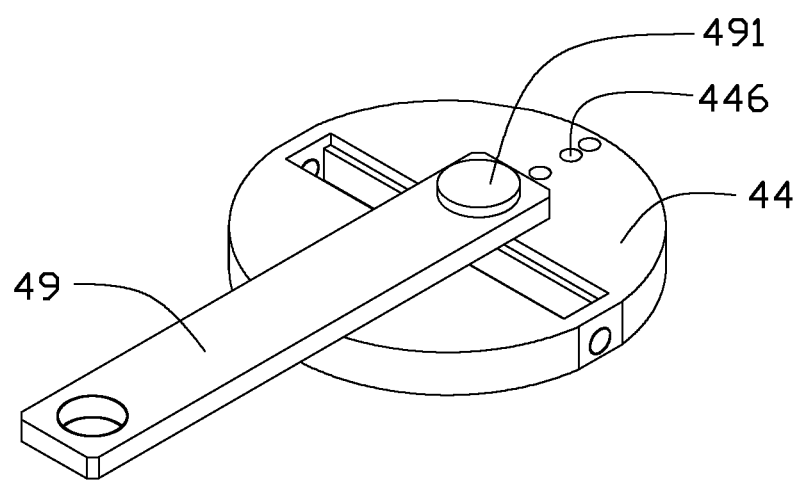
FIG. 4 is an assembled view, showing the connecting plate attached to the rotational plate according to one embodiment.
Figure 5:
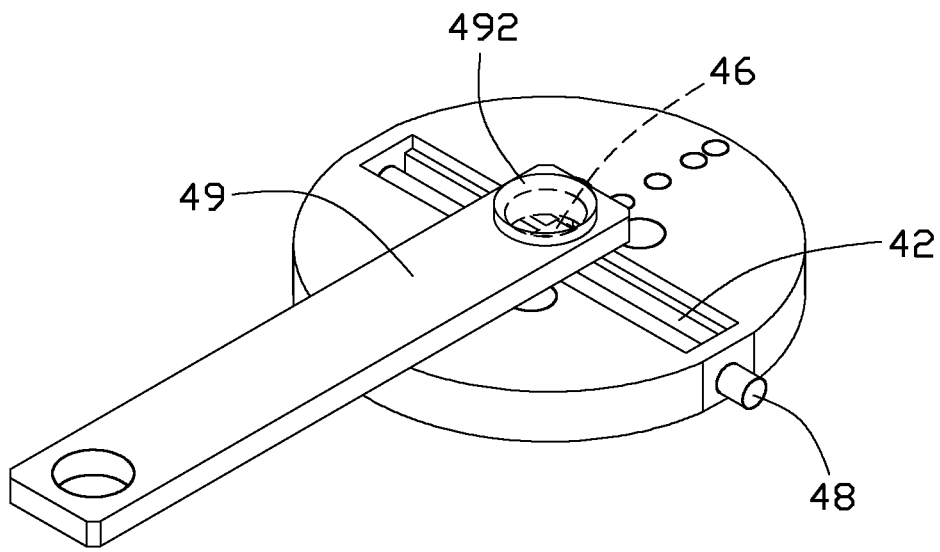
FIG. 5 is an assembled view, showing the connecting plate attached to the rotational plate according to another embodiment.

The connecting plate 49 is attached to the rotational plate 44. Referring to FIG. 4, one end of the connecting plate 49 can be mounted to the rotational plate 44 by means of a first screw 491 extending through any adjusting hole 446. Since the distance of each adjusting hole 446 from the center of the rotational plate 44 is different the movement trace of the connecting plate 49 is determined by which adjusting hole 446 is used. In another embodiment, referring to FIG. 5, one end of the connecting plate 49 is mounted on the nut 46 by the engagement of a second screw 492 and the latching hole 464. When the lateral position of the nut 46 is changed, the stroke of the connecting plate 49 accordingly changes. Thus the connecting plate 49 can be made to move either by means of the adjusting holes 446 or by means of the latching hole 462, so providing an extreme degree of adaptability in the ranges of movement of the frictional members 70.

The sliding module 50 includes two guiding rails 52, two sliding blocks 54, and a support plate 56. The guiding rails 52 are mounted on the top plate 12, and the sliding blocks 54 are slidably engaged in the guiding rails 52. The sliding blocks 54 are mounted to the two sides of the support plate 56. The other end of the connecting plate 49 is mounted to the middle portion of one side of the support plate 56. Since the rotational plate 44 moves the connecting plate 49 and the guiding rails 52 cannot rotate, the connecting plate 49 drives the support plate 56 and the sliding blocks 54 to slide in a reciprocating manner relative to the guiding rails 52.

Figure 6:
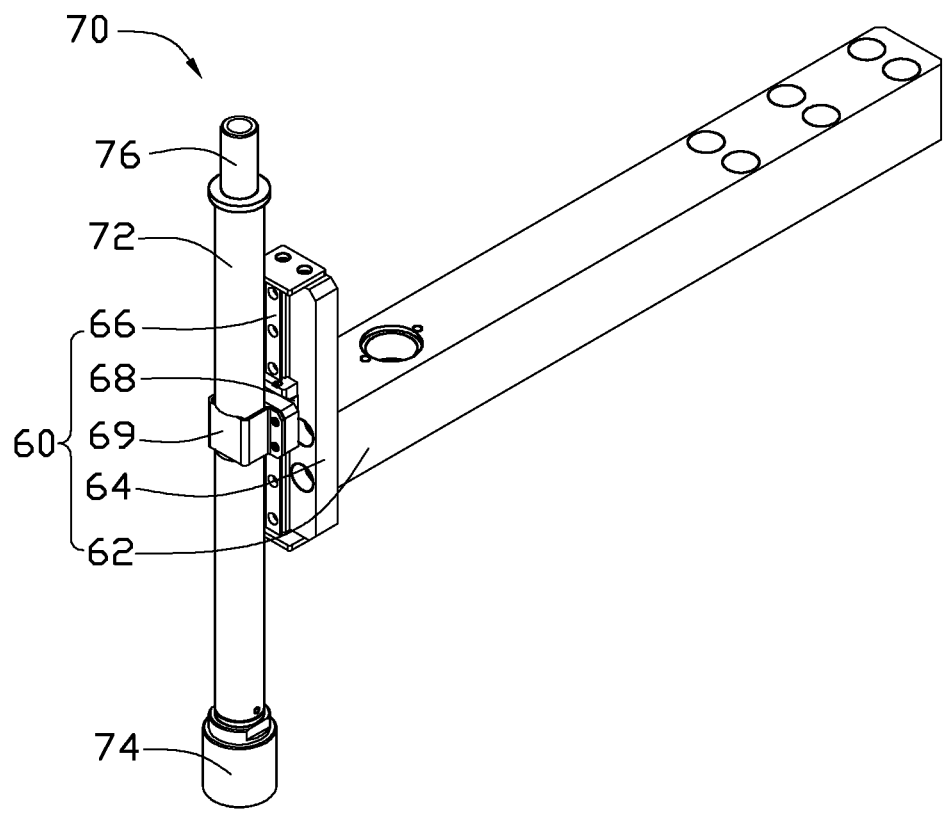
FIG. 6 is an enlarged view of an assembled connecting module attached to a frictional member as contained in FIG. 2.

Referring to FIG. 6, each connecting module 60 causes the frictional members 70 to move backwards and forwards repeatedly. Each connecting module 60 includes a beam 62, a main section 64, a guiding block 66, a seat 68, and a holding member 69. The beam 62 is connected to one end of the main section 64. One end of the beam 62 is fixed to the support plate 56. The guide block 66 is formed at one side of the main section 64 opposite to the beam 62. The seat 64 is slidably engaged with the guide block 66. The holding member 69 is mounted to the seat 68 and clamps a frictional member 70

Each frictional member 70 includes a rod body 72, a frictional head 74 and a counterweight 76. The holding member 69 is clamped to the rod body 72. The frictional head 74 is formed at the lower end of the rod body 72. The counterweight 76 is positioned at the opposite end of the rod body 72 for adjusting the amount of pressure applied by the frictional head 74 to the tested product.

During testing, the tested products are held in the clamping members 22, the frictional members 70 extend through the holding members 69, and are positioned on the connecting modules 60. The height of each frictional member 70 can be adjusted in the seat 68 according to the height required for the tested product, and in addition, the stroke of the connecting plate 49 is fully adjustable for testing different products It is to be understood that even though numerous characteristics and advantages of the present embodiments have been set forth in the foregoing description, together with details of structures and functions of various embodiments, the disclosure is illustrative only, and changes may be made in detail, especially in the matters of shape, size, and arrangement of parts within the principles of the present invention to the full extent indicated by the broad general meaning of the terms in which the appended claims are expressed.

What is claimed is:

1. A testing module, comprising:
   a main body;
   a drive module positioned in the main body,
   a sliding module;
   a transmission module including a rotational plate and a connecting plate, the drive module driving the rotational plate to rotate; one end of the connecting plate attached to the sliding module, and the other end thereof adjustably attached to the rotational plate; and
   a frictional member mounted to the sliding module;
   wherein a groove is diametrically defined along the rotational plate, and is shorter than the overall diameter of the rotational plate.

2. The testing module as claimed in claim 1, wherein a number of adjusting holes are defined in the rotational plate, and the adjusting holes are arranged along a line and at different distances from a center of the plate.

3. The testing module as claimed in claim 1, further comprising a support ring, wherein the support ring is attached to the main body, and the rotational plate is disposed on the support ring.

4. The testing module as claimed in claim 1, wherein a through hole is defined at each side of the rotational plate, and communicates with opposite ends of the groove.

5. The testing module as claimed in claim 4, further comprising a nut and a bolt, wherein the nut is slidably received in the groove, the bolt is inserted into the through hole and the groove, and is screwed into the nut.

6. The testing module as claimed in claim 5, wherein the nut is substantially T-shaped, and defines a threaded hole and a latching hole, the axis of the threaded hole is parallel with the groove and perpendicular to that of the latching hole, the bolt is inserted into the through hole and the groove, and is screwed into the threaded hole.

7. A testing module, comprising:
   a main body;
   a drive module positioned in the main body,
   a sliding module;
   a transmission module including a rotational plate and a connecting plate, the drive module driving the rotational plate to rotate; one end of the connecting plate attached to the sliding module, and the other end thereof adjustably attached to the rotational plate;
   a support ring attached to the main body, and the rotational plate disposed on the support ring; and
   a frictional member mounted to the sliding module;
   wherein a groove is diametrically defined along the rotational plate, and is shorter than the overall diameter of the rotational plate.

8. The testing module as claimed in claim 7, wherein a through hole is defined at each side of the rotational plate, and communicates with opposite ends of the groove.

9. The testing module as claimed in claim 8, further comprising a nut and a bolt, wherein the nut is slidably received in the groove, the bolt is inserted into the through hole and the groove, and is screwed into the nut.

10. The testing module as claimed in claim 9, wherein the nut is substantially T-shaped, and defines a threaded hole and a latching hole, the axis of the threaded hole is parallel with the groove and perpendicular to that of the latching hole, the bolt is inserted into the through hole and the groove, and is screwed into the threaded hole.

* * * * *